United States Patent [19]

Takaya et al.

[11] Patent Number: 4,962,230
[45] Date of Patent: Oct. 9, 1990

[54] PROCESS FOR PRODUCING OPTICALLY ACTIVE CARBOXYLIC ACID

[75] Inventors: Hidemasa Takaya; Tetsuo Ohta; Ryoji Noyori, all of Aichi; Noboru Sayo, Kanagawa; Hidenori Kumobayashi, Kanagawa; Susumu Akutagawa, Kanagawa, all of Japan

[73] Assignee: Takasago International Corporation, Tokyo, Japan

[21] Appl. No.: 121,247

[22] Filed: Nov. 16, 1987

[30] Foreign Application Priority Data

Nov. 14, 1986 [JP] Japan ................... 61-269589
Jul. 31, 1987 [JP] Japan ................... 62-192339

[51] Int. Cl.$^5$ .......................... C07C 229/42
[52] U.S. Cl. ..................... 562/433; 562/441; 562/452; 562/456; 562/457; 562/466; 562/468; 562/478; 562/465; 562/490; 562/491; 562/496; 562/598; 562/606
[58] Field of Search .............. 562/633, 441, 452, 456, 562/457, 466, 468, 478, 465, 490, 491, 496, 598, 606

[56] References Cited

U.S. PATENT DOCUMENTS

| | | | |
|---|---|---|---|
| 4,328,364 | 5/1982 | Mazzei et al. | 562/433 |
| 4,440,936 | 4/1984 | Riley | 562/433 |
| 4,504,674 | 3/1985 | McKinney | 562/598 |
| 4,613,680 | 9/1986 | Naruto et al. | 562/598 |
| 4,739,084 | 4/1988 | Takaya et al. | 556/21 |
| 4,739,085 | 4/1988 | Takaya et al. | 556/21 |

FOREIGN PATENT DOCUMENTS 0174057 3/1986 European Pat. Off. .
245959 11/1987 European Pat. Off. .
256634 2/1988 European Pat. Off. .

OTHER PUBLICATIONS

Chemical Abstract, 92:725 (Feb. 1980), Abstract No. 41289u.
*Tetrahedron Letters* No. 29, pp. 2487–2490, 1977, "Asymmetric Homogeneous Hydrogenation with Phosphine-Rhodium Complexes Chiral Both at Phosphorus and Carbon", Fisher et al.
Journal of Molecular Catalysis 5(1979) 41–50 "Hydrogenation Asymetrique en 'Presence de Diphoshines Chirales'", P. Aviron-Violet, et al.
The Chemical Society of Japan, Bull. Chem Soc. Jpn. 55, 2917–2921 (1982), "Synthesis of Sugar Derivatives of Tervalent Phosphorus Compounds and Their Application to Homogeneous Assymetric Hydrogenation," Yamashita, et al.
"Synthesis of Novel Chiral Ruthenium Complexes of 2,2'-Bis(diphenylphosphino)-1,1'-binaphthyl and Their use as Asymmetric Catalysts", Journal Chem. Soc. Commun., 1985, I. Ikrariya, et al.

*Primary Examiner*—Bruce Gray
*Attorney, Agent, or Firm*—Sughrue, Mion, Zinn, Macpeak & Seas

[57] ABSTRACT

A process for producing an optically active carboxylic acid represented by formula (I):

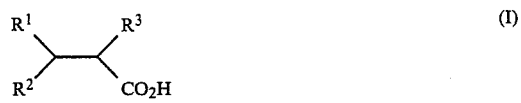

(I)

wherein $R^1$, and $R^2$, and $R^3$ each represents a hydrogen atom, an alkyl group, an alkenyl group, or a phenyl or naphthyl group which may have a substituent, provided that all of $R^1$, $R^2$, and $R^3$ are not simultaneously a hydrogen atom; when $R^1$ and $R^2$ are simultaneously a hydrogen atom, then $R^3$ is not a methyl group; and that when $R^3$ is a hydrogen atom, then $R^1$ and $R^2$ are each a group other then a hydrogen atom, is disclosed, comprising asymmetrically hydrogenating an $\alpha,\beta$-unsaturated carboxylic acid represented by formula (II):

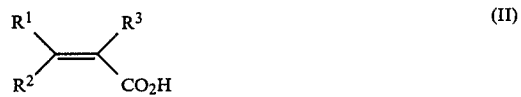

(II)

wherein $R^1$, $R^2$, and $R^3$ are the same as defined above, in the presence of a ruthenium-optically active phosphine complex as a catalyst.

7 Claims, No Drawings

PROCESS FOR PRODUCING OPTICALLY ACTIVE CARBOXYLIC ACID

FIELD OF THE INVENTION

This invention relates to a process for producing an optically active carboxylic acid by asymmetric synthesis. More particularly, the invention relates to a process for producing an optically active carboxylic acid represented by formula (I):

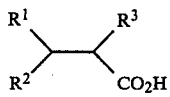

wherein $R^1$, $R^2$, and $R^3$ each represents a hydrogen atom, an alkyl group, an alkenyl group, or a phenyl or naphthyl group which may have a substituent, provided that all of $R^1$, $R^2$, and $R^3$ are not simultaneously a hydrogen atom; when $R^1$ and $R^2$ are simultaneously a hydrogen atom, then $R^3$ is not a methyl group; and that when $R^3$ is a hydrogen atom, then $R^1$ and $R^2$ are each a group other than a hydrogen atom,
which process comprises asymmetrically hydrogenating an $\alpha,\beta$-unsaturated carboxylic acid represented by formula (II):

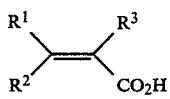

wherein $R^1$, $R^2$, and $R^3$ are the same as defined above, in the presence of a ruthenium-optically active phosphine complex as a catalyst.

BACKGROUND OF THE INVENTION

The optically active carboxylic acids shown by formula (I) have been watched with keen interest as raw materials for synthesizing various useful materials, for example, as intermediates for synthesizing physiologically active substances of natural materials and also as liquid crystal materials.

Several methods of asymmetric synthesis have been available for producing such optically active carboxylic acids, for example, (1) a method starting with naturally occurring optically active isomers; (2) a method utilizing microbial asymmetric hydrogenation; and (3) a method involving asymmetric hydrogenation in the presence of a specified catalyst.

In particular, as the process for producing the optically active carboxylic acid of formula (I) from the $\alpha,\beta$-unsaturated carboxylic acid of formula (II) by asymmetric synthesis, a process in which the $\alpha,\beta$-unsaturated carboxylic acid is asymmetrically hydrogenated in the presence of a rhodium-optically active phosphine complex as a catalyst is reported. That is, C. Fisher et al report in *Tetrahedron Letters*, 29, pp. 2487 to 2490 (1977) that 2-methylphenylacetic acid is obtained in an optical yield of 27.5% ee by asymmetric hydrogenation of atropic acid (2-methylenephenylacetic acid). Also, P. Aviron-Violet et al report asymmetric hydrogenation of atropic acid in an optical yield of 70% ee in *J. Mol. Cat.*, 5, pp. 41 to 50 (1979). Furthermore, M. Yamashita et al report in *Bull. Chem. Soc. Jon.*, 55, pp. 2917 to 2921 (1982) that 2-methylbutyric acid is obtained by asymmetric hydrogenation of tiglic acid ((E)-2-methyl-2butenoic acid) in an optical yield of 62% ee.

Among these methods of asymmetric synthesis, according to the method (1) starting with naturally occurring optically active isomers or method (2) utilizing microbial asymmetric hydrogenation, though desired carboxylic acids with high optical purities can be obtained, not only the absolute configuration of the resulting optically active carboxylic acids is limited to a specific one, but also it is difficult to synthesize their enantiomers. Further, in accordance with the asymmetric hydrogenation of $\alpha,\beta$-unsaturated carboxylic acid derivatives using a rhodium-optically active phosphine catalyst, not only the optical purities of the resulting carboxylic acids are not yet satisfactory, but also since metallic rhodium to be used is expensive due to limitations in place and quantity of production when used as a catalyst component, it forms a large proportion in cost of the catalyst, ultimately resulting in an increase in cost of the final commercial products.

SUMMARY OF THE INVENTION

In order to solve the aforesaid problems, the present inventors have conducted intensive studies and eventually found that when asymmetric hydrogenation is carried out using, as a catalyst, a relatively cheap ruthenium-optically active phosphine catalyst, the desired carboxylic acid with a high optical purity can be obtained.

An object of the present invention is, therefore, to provide a process for producing an optically active carboxylic acid represented by formula (I):

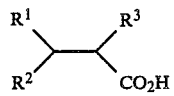

wherein $R^1$, $R^2$, and $R^3$ each represents a hydrogen atom, an alkyl group, an alkenyl group, or a phenyl or naphthyl group which may have a substituent, provided that all of $R^1$, $R^2$, and $R^3$ are not simultaneously a hydrogen atom; when $R^1$ and $R^2$ are simultaneously a hydrogen atom, then $R^3$ is not a methyl group; and that when $R^3$ is a hydrogen atom, then $R^1$ and $R^2$ are each a group other than a hydrogen atom, which process comprises asymmetrically hydrogenating an $\alpha,\beta$-unsaturated carboxylic acid represented by formula (II):

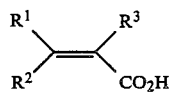

wherein $R^1$, $R^2$, and $R^3$ are the same as defined above, in the presence of a ruthenium-optically active phosphine complex as a catalyst.

DETAILED DESCRIPTION OF THE INVENTION

The process of this invention is performed as follows.

That is, an $\alpha,\beta$-unsaturated carboxylic acid of formula (II) is dissolved in a protic solvent such as methol, ethanol, and methyl cellosolve. Depending upon the type of substrate used, an equimolar amount of a tertiary amine such as triethylamine, dicyclohexylmethylamine, and tri-n-butylamine is appropriately selected and added thereto, and the mixture is placed in an autoclave.

Thereafter, a ruthenium optically active phosphine complex is added to the mixture in an amount of from 1/100 to 1/3000 mole per mole of the α, β-unsaturated carboxylic acid, and hydrogenation is performed for from one to 100 hours at a hydrogenation temperature of from 0° C. to 80° C. under a hydrogen pressure of from 4 kg/cm² to 135 kg/cm². After completion of the reaction, the solvent is distilled off and, then, the residue is distilled under reduced pressure to provide the desired optically active carboxylic acid of formula (I) in an almost quantitative yield.

In formula (II) which represents the α, β-unsaturated carboxylic acid used as a raw material in this invention, $R^1$, $R^2$, and $R^3$ each represents a hydrogen atom, an alkyl group (e.g., those having from 1 to 7 carbon atoms), an alkenyl group (e.g., those having from 3 to 6 carbon atoms), or a phenyl or naphthyl group which may have a substituent (e.g., a hydroxyl group, a methoxy group, an amino group, a dimethylamino group, a chlorine atom, and a bromine atom), or an aryl group which may have a substituent, provided that all of $R^1$, $R^2$, and $R^3$ are not simultaneously a hydrogen atom; when $R^1$ and $R^2$ are simultaneously a hydrogen atom, then $R^3$ is not a methyl group; and that when $R^3$ is a hydrogen atom, then $R^1$ and $R^2$ are a group other than a hydrogen atom. The abovedescribed condition is to be provided such that the carbon atom at the α-position or β-position of the carboxylic acid of formula (I) obtained by the process of this invention be an asymmetric carbon atom to exhibit optical activity.

Examples of the α, β-unsaturated carboxylic acid of formula (II) are tiglic acid, angelic acid ((Z)-2-methyl-2-butenoic acid), 2-methyl-2-pentenoic acid, atropic acid (2-methylenephenylacetic acid), p-hydroxy atropic acid, p-methoxy atropic acid, p-chloro atropic acid, p-bromo atropic acid, p-amino atropic acid, p-dimethylamino atropic acid, 3-methyl-2,5-hexadienoic acid, geranic acid, 2-methylenenonanoic acid, 2-methylcinnamic acid, 3-methylcinnamic acid, 2-phenylcinnamic acid, and 6-methoxy-α-methylene-2- naphthaleneacetic acid.

Examples of the ruthenium-optically active phosphine complex which can be used as the catalyst in the present invention are those as described below. In the following examples, the abbreviations as designated below are used.

| | |
|---|---|
| Et: | Ethyl group |
| Bu: | Butyl group |
| t-Bu: | t-Butyl group |
| i-Pr: | Isopropyl group |
| Ph: | Phenyl group |
| BINAP: | 2,2'-Bis(diphenylphosphino)-1,1'-binaphthyl |
| T-BINAP: | 2,2'-Bis(di-p-tolylphosphino)-1,1'-binaphthyl |
| t-BuBINAP: | 2,2'-Bis(di-p-t-butylphenylphosphino)-1,1'-binaphthyl |
| sulfonated BINAP: | 2,2'-Bis(diphenylphosphino)-5,5'-bis-(sodium sulfonate)-1,1'-binaphthyl |
| amino BINAP: | 2,2'-Bis(diphenylphosphino)-5,5'-bis-(amino)-1,1'-binaphthyl |
| acetylamino BINAP: | 2,2'-Bis(diphenylphosphino)-5,5'-bis-(acetylamino)-1,1'-binaphthyl |

$$Ru_xH_yCl_z(R^4\text{-BINAP})_2(Q)_p \quad (III)$$

wherein $R^4$-BINAP signifies a tertiary phosphine of formula (IV):

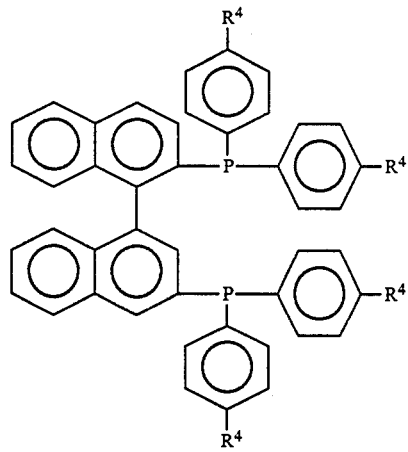

in which $R^4$ is a hydrogen atom or a methyl group; Q is a tertiary amine; when y is 0, then x is 2, z is 4, and p is 1; and when y is 1, then x is 1, z is 1, and p is 0.

Examples of the tertiary amine for Q include triethylamine, tri-n-butylamine, tri-n-octylamine, N-methylpiperidine, N-methylpyrrolidine, N-methylmorpholine, pyridine, dimethylaniline, and tetramethylethylenediamine.

The ruthenium-optically active phosphine complex of formula (III) can be obtained by the methods described in T. Ikariya et al, *J. Chem. Soc., Chem. Commun.*, pp. 922–924 (1985) and European Patent No. 174,057A. That is, in the case of y=0, ruthenium chloride is reacted with cycloocta-1,5-diene (abbreviated as "COD") in an ethanol solution to form [RuCl₂(COD)]ₙ, and one mole of this complex is reacted with 1.2 moles of $R^4$-BINAP under heating in a solvent such as toluene or ethanol in the presence of 4 moles of a tertiary amine such as triethylamine.

Further, in the case of y=1, one mole of [RuCl₂(COD)]ₙ is reacted with 2.25 moles of $R^4$-BINAP and 4.5 moles of a tertiary amine.

If an optically active form of $R^4$-BINAP is used in the above-described method, a ruthenium-phosphine complex having corresponding optically active properties can be obtained.

Specific examples of the ruthenium-optically active phosphine complex are listed below:

Ru₂Cl₄(BINAP)2(NEt₃);
Ru₂Cl₄(T-BINAP)₂(NEt₃);
RuHCl(BINAP)₂;
RuHCL(T-BINAP)₂;
Ru₂Cl₄(t-BuBINAP)₂(NEt₃);
Ru₂Cl₄(BINAP)₂(NBu₃); and

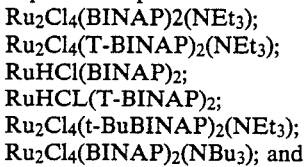

(V)

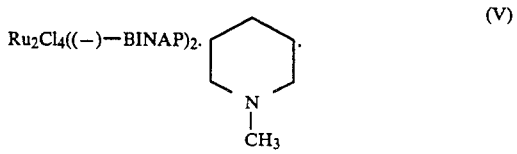

wherein X-$R^5$-BINAP signifies a tertiary phosphine of formula (VI):

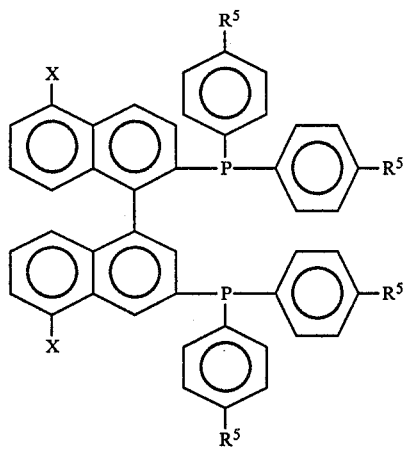

(VI)

in which X represents a hydrogen atom, an amino group, an acetylamino group, or a sulfo group;

$R^5$ represents a hydrogen atom or a lower alkyl group (e.g., those having from 1 to 4 carbon atoms); $R^6$ and $R^7$ each represents an alkyl group (e.g., those having from 1 to 9 carbon atoms), a halogenated lower alkyl group (e.g., those having from 1 to 4 carbon atoms; examples of the halogen include fluorine, chlorine, and bromine), a phenyl group, a phenyl group substituted with a lower alkyl group (e.g., those having from 1 to 4 carbon atoms), an α-aminoalkyl group (e.g., those having from 1 to 4 carbon atoms), or an α-aminophenylalkyl group (e.g., those having from 7 to 10 carbon atoms), or $R^6$ and $R^7$ are taken together to form an alkylene group (e.g., those having from 1 to 4 carbon atoms); and q represents 1 or 2.

The complex of formula (V) can be prepared in accordance with the method as disclosed in Japanese Patent Application No. 108888/1986 (corresponding to U.S. application Ser. No. 38,570, filed Apr. 15, 1987). That is, $Ru_2Cl_4(X-R^5-BINAP)_2(NEt_3)$ as a starting material is reacted with a carboxylic acid salt in an alcoholic solvent such as methanol, ethanol, or t-butanol at a temperature of from about 20 to 110° C. for a period of time of from 3 to 15 hours; after distilling off the solvent, the desired complex is extracted with a solvent such as diethyl ether or ethanol; and the extract is evaporated to dryness to obtain a crude complex which is then recrystallized from a suitable solvent such as ethyl acetate, whereby a purified product can be obtained.

Also, a complex having a trifluoroacetate group can be obtained by reacting a diacetate complex, $Ru(X-R^5-BINAP)(O_2CCH_3)_2$ obtained by the manner as described above and trifluoroacetic acid using methylene chloride as a solvent for about 12 hours at about 25° C.

Furthermore, in the case of producing the complex having two equivalents of ligands coordinated to the ruthenium metal, that is, the complex of formula (V) wherein q is 2, $RuHCl(X-R^5-BINAP)_2$ obtained by the abovedescribed manner is reacted with a carboxylate in a solvent such as methylene chloride.

If an optically active form of $X-R^5$-BINAP is used in the method described above, a ruthenium-phosphine complex of formula (V) having corresponding optically active properties can be obtained.

Specific examples of the complex of formula (V) are listed below:

$Ru(BINAP)(O_2CCH_3)_2$;
$Ru(BINAP)(O_2CCF_3)_2$;
$Ru(T-BINAP)_2(O_2CCF_3)_2$;
$Ru(T-BINAP)_2(O_2CCH_3)_2$;
$Ru(BINAP)(O_2Ct-Bu)_2$;
$Ru(BINAP)(O_2CPh)_2$;
$Ru(T-BINAP)(O_2CCH_3)_2$;

$Ru(T-BINAP)(O_2CCF_3)_2$;
$Ru(t-BuBINAP)(O_2CCH_3)_2$;
$Ru(amino\ BINAP)(O_2CCH_3)_2$;
$Ru(acetylamino\ BINAP)(O_2CCH_3)_2$;
$Ru(sulfonated\ BINAP)(O_2CCH_3)_2$;

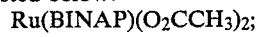

(VII)

$Ru(BINAP)(O_2CCHCH_2Ph)_2$; and
                   |
                   NH$_2$ $Ru(BINAP)(O_2CCH$-$i$-$Pr)_2$.
                 |
                NH$_2$ (3) $[RuH_l(R^4$—$BINAP)_v]Y_w$ wherein $R^4$-BINAP signifies a tertiary phosphine of formula (IV) described above; Y is $ClO_4$, or $PF_6$; when $l$ is 0, then v is 1 and w is 2; and when l is 1, then v is 2 and w is 1.

The complex of formula (VII) can be prepared in accordance with the method as disclosed in Japanese Patent Application No. 184651/1986 (corresponding to U.S. application Ser. No. 61,770, filed June 15, 1987).

That is, a complex of formula (VII) wherein l is 0, v is 1, and w is 2 is produced by reacting, as a starting compound, $Ru_2Cl_4(R^4$-$BINAP)_2(NEt_3)$ with a salt represented by formula (VIII):

$$MY \qquad (VIII)$$

wherein M is a metal selected from the group consisting of Na, K, Li, Mg, and Ag; and Y is $ClO_4$, $BF_4$, or $PF_6$, in a solvent composed of water and methylene chloride in the presence of, as a phase transfer catalyst, a quaternary ammonium salt or a quaternary phosphonium salt represented by formula (IX):

$$R^8R^9R^{10}R^{11}AB \qquad (IX)$$

wherein $R^8$, $R^9$, $R^{10}$, and $R^{11}$ are each an alkyl group having from 1 to 16 carbon atoms, a phenyl group, or a benzyl group; A is nitrogen or phosphorus; and B is a halogen (e.g., chorine, iodine, or bromine).

The reaction between $Ru_2Cl_4(R^4$-$BINAP)_2(NEt_3)$ and the salt of formula (VIII) is carried out by adding these two compounds and the phase transfer catalyst of formula (IX) in a mixed solvent of water and methylene chloride and stirring the mixture. The salt of formula (VIII) is used in an amount of from 2 to 10 moles and preferably 5 moles per mole of the ruthenium, and the phase transfer catalyst of formula (IX) is used in an amount of from 1/100 to 1/10 mole per mole of the ruthenium, respectively. It suffices to continue the stirring for a period of time of from 6 to 18 hours and typically 12 hours at a temperature of from 5° to 30° C.

Examples of the salt of formula (VIII) include perchlorates, borofluorides, and hexafluorophosphates of Na, K, Li, Mg, or Ag. Compounds useful as the phase transfer catalyst of formula (IX) are found in documented references, such as W. P. Weber and G. W. Gokel, *Phase Transfer Catalysis in Organic Synthesis*, Springer-Verlag, pp. 6 (1977).

After completion of the reaction, the reaction mixture is allowed to stand, and the methylene chloride solution separated from the aqueous layer is washed and stripped of the methylene chloride by evaporation under vacuum so as to obtain the end product.

Alternatively, the end compound can be synthesized by reacting Ru(R$^4$-BINAP)(O$_2$CCH$_3$)$_2$ with an acid represented by formula (X):

$$HY \qquad (X)$$

wherein Y is ClO$_4$, BF$_4$, or PF$_6$,
under stirring in a mixed solvent of methylene chloride and methanol. The acid of formula (X) is used in an amount of from 2 to 6 moles and preferably 4 moles per mole of the ruthenium. It suffices to continue the stirring for a period of time of from 6 to 18 hours and typically 12 hours at a temperature of from 5° to 30° C.

A complex of formula (VII) wherein l is 1, v is 2, and w is 1 can be produced by reaction of, as a starting material, RuHCl(R$^4$-BINAP)$_2$ with the salt of formula (VIII) in a mixed solvent of water and methylene chloride in the presence of the phase transfer catalyst of formula (IX). The salt of formula (VIII) is used in an amount of from 2 to 10 moles and preferably 5 moles per mole of the ruthenium, and the phase transfer catalyst of formula (IX) is used in an amount of from 1/100 to 1/10 mole per mole of the ruthenium. It suffices to continue the stirring for a period of time of from 6 to 18 hours and typically 12 hours at a temperature of from 5 to 30° C.

Specific examples of the complex of formula (VII) are listed below:
[Ru(T-BINAP)](BF$_4$)$_2$;
[RuH(T-BINAP)$_2$]BF$_4$;
[Ru(BINAP)](BF$_4$)$_2$;
[Ru(BINAP)](ClO$_4$)$_2$;
[Ru(T-BINAP)](ClO$_2$)$_2$;
[Ru(T-BINAP)](PF$_6$)$_2$;
[RuH(BINAP)$_2$]BF$_4$;
[RuH(T-BINAP)$_2$]ClO$_4$; and
[RuH(T-BINAP)$_2$]PF$_6$.

The present invention is hereunder described in greater detail by way of Referential Examples and Examples which, however, should not be taken as limiting. Analyses were conducted in these examples with the following instruments:

Gas chromatography: Shimadzu GC-9A (made by Shimadzu Seisakusho, Ltd.)
  Column: OV-101 silica capillary (0.25 mm$\phi$ × 25 m$^L$, made by Gasukuro Kogyo Inc.), with the temperature being increased from 100 to 250° C. at a rate of 3° C./min High-performance liquid chromatography: Hitachi Liquid Chromatograph 655A-11 (made by Hitachi, Ltd.)
  Column: Chemcopack Nucleosil 100-3 (4.6 mm$\phi$ × 300 mmL, made by Chemco Co., Ltd.)
  Solvent: hexane/diethyl ether (7:3 by volume) at a flow rate 1 ml/min
  Detector: UV Detector 635M (UV-254) (made by Hitachi, Ltd.)

$^1$H NMR spectrometer: Model JNM-GX400 (400MHz) (made by JEOL Ltd.)
  Internal standard: tetramethylsilane Polarimeter: Polarimeter DIP-4 (made by Japan Spectroscopic Co., Ltd.)

$^-$P NMR spectrometer: Model JNM-GX400 (161 MHZ) (made by JEOL Ltd.), with chemical shifts being determined with 85% phosphoric acid used as an external standard Referential Example 1

Preparation of Ru$_2$Cl$_4$((−)−T−BINAP)$_2$(NEt$_3$):

In a 250 ml Schlenk's tube were placed 1 g (3.6 mmoles) of [RuCl2(COD)]n and 2.9 g (4.3 mmoles) of (−)−T−BINAP. After sufficiently replacing the inside atmosphere of the tube with nitrogen, 1.5 g of triethylamine and 50 ml of toluene were added thereto, and the resultant mixture was heated under reflux for 6 hours to perform reaction. After completion of the reaction, the solvent was distilled off under reduced pressure.

Crystals thus formed were recovered and dissolved in methylene chloride, and the solution was filtered on Celite. The filtrate was concentrated to dryness to provide 3.6 g of Ru$_2$Cl$_4$((−)−T−BINAP)$_2$(NEt$_3$) as a dark red solid in a yield of 100%.

Elemental Analysis for C$_{102}$H$_{95}$Cl$_4$NP$_4$Ru$_2$:

|  | Ru | C | H | P |
| --- | --- | --- | --- | --- |
| Calculated: | 11.21% | 67.96% | 5.31% | 6.87% |
| Found: | 10.97% | 67.51% | 5.88% | 6.46% |
| $^{31}$P NMR (CDCl$_3$) δppm: | 49.65 (s), 49.89 (s), 51.07 (s), 51.30 (s). | | | |

Referential Example 2

Preparation of RuHCl((+)-BINAP)$_2$:

In a 250 ml Schlenk's tube were placed 0.5 g (1.8 mmoles) of [RuCl$_2$(COD)]$_n$ and 2.6 g (4.1 mmoles) of (+)-BINAP. After sufficiently replacing the inside atmosphere of the tube with nitrogen, 0.8 g (8 mmoles) of triethylamine and 50 ml of ethanol were added thereto, and the resultant mixture was heated under reflux for 6 hours to perform reaction. After completion of the reaction, the ethanol was distilled off under reduced pressure, and the residue was dried to provide 2.8 g of RuHCl((+)-BINAP)$_2$ as yellow crystals. The yield was 100%.

Elemental Analysis for C$_{88}$H$_{65}$ClP$_4$Ru:

|  | Ru | C | H | P |
| --- | --- | --- | --- | --- |
| Calculated: | 7.31% | 76.43% | 4.74% | 8.96% |
| Found: | 6.95% | 76.17% | 5.15% | 8.67% |
| $^{31}$P NMR (CDCl$_3$) δppm: | 21.90 (t, J = 0.83 Hz), 37.74 (t, J = 0.83 Hz) | | | |

Referential Example 3

Preparation of Ru((−)−BINAP)(O$_2$CCH$_3$)$_2$:

In a 250 ml Schlenk's tube were placed 1.43 g (0.9 mmole) of Ru$_2$Cl$_4$((−)−BINAP)$_2$(NEt$_3$) prepared according to the same manner as in Referential Example 1 except using (−)−BINAP in place of (−)−T−BINAP and 3.06 g (37 mmoles) of sodium acetate. After sufficiently replacing the inside atmosphere of the tube with nitrogen, 100 ml of t-butanol was added thereto, and the resultant mixture was heated under reflux for 12 hours to perform reaction. After completion of the reaction, the t-butanol was distilled off under a reduced pressure of 20 mmHg to dryness, and the residue was extracted twice with 10 ml of diethyl ether. The diethyl ether was distilled off to dryness, and solids thus obtained were further extracted twice with 10 ml of ethanol. The extract was concentrated to dryness to provide 1.5 g of crude Ru((−)-−BINAP)-(O$_2$CCH$_3$)$_2$. The product was further recrystallized from ethyl acetate to provide 0.79 g of a yellowish brown solid. The yield was 52%.

Melting Point: 180-181° C. (decomposed)
Elemental Analysis for C$_{48}$H$_{38}$O$_4$P$_2$Ru:

|  | Ru | P | C | H |
|---|---|---|---|---|
| Calculated: | 12.01% | 7.36% | 68.48% | 4.55% |
| Found: | 11.85% | 7.28% | 68.35% | 4.61% |
| $^{31}$P NMR (CDCl$_3$) δppm: | 65.00 (s) | | | |
| $^1$H NMR (CDCl$_3$) δppm: | 1.75 (s, 6H, OCCH$_3$ with O double bond),<br>6.5-7.8 (m, 32H, naphthyl ring and phenyl proton). | | | |

Referential Example 4

Preparation of Ru((−)−T−BINAP)(O$_2$CCF$_3$)$_2$:

In a 250 ml Schlenk's tube, the inside atmosphere of which had previously been replaced with nitrogen, was placed 0.74 g (0.82 mmole) of Ru((−)−T−BINAP)-(O$_2$CCH$_3$)$_2$ prepared according to the same manner as in Referential Example 3 except using (−)−T−BINAP in place of (−)−BINAP and 10 ml of methylene chloride was added thereto to form a homogeneous solution. Then, 0.14 ml (1.81 mmoles) of trifluoroacetic acid was added to the solution, and the mixture was stirred for 12 hours at room temperature. After completion of the reaction, the reaction mixture was concentrated to dryness to provide 0.7 g of Ru((-)-T-BINAP) (O$_2$CCF$_3$)$_2$ as a brown solid. The yield was 91%.

Elemental Analysis for C$_{52}$H$_{40}$F$_6$O$_4$P$_2$Ru:

|  | Ru | C | H | P |
|---|---|---|---|---|
| Calculated: | 10.05% | 62.09% | 4.01% | 6.16% |
| Found: | 9.89% | 62.27% | 4.15% | 5.82% |
| $^{31}$P NMR (CDCL$_3$) δppm: | 59.91 (s) | | | |

Referential Example 5

Preparation of [Ru((-)-BINAP)](BF$_4$)$_2$:

In a Schlenk's tube was placed 0.51 g (0.61 mmole) of Ru((−)−BINAP)(O$_2$CCH$_3$)$_2$ obtained in Referential Example 3. After sufficiently replacing the inside atmosphere of the tube with nitrogen, 7 ml of methylene chloride, 7 ml of methanol, and 0.52 ml (2.48 mmoles) of an aqueous solution of 42% borofluoric acid were added thereto, and the mixture was stirred for 12 hours at room temperature. Thereafter, the reaction mixture was concentrated under reduced pressure to provide 0.53 g of [Ru((−)−BINAP)-(BF$_4$)$_2$ as a brown solid. The yield was 97.2%.

Elemental Analysis for C$_{44}$H$_{32}$B$_2$F$_8$P$_2$Ru:

|  | Ru | P | C | H |
|---|---|---|---|---|
| Calculated: | 11.26% | 6.90% | 58.90% | 3.59% |
| Found: | 10.88% | 6.51% | 58.62% | 3.82% |
| $^{31}$P NMR (CDCl$_3$) δppm: | 10.357 (d, J = 48.9 Hz),<br>77.450 (d, J = 48.9 Hz) | | | |

Referential Example 6

Preparation of [Ru((+)−T−BINAP)](ClO$_4$)$_2$;

In a 250 ml Schlenk's tube was placed 0.54 g (0.3 mmole) of Ru$_2$Cl$_4$(+)−T−bINAP)$_2$(NEt$_3$) prepared according to the same manner as in Referential Example 1 except using (+)−T−BINAP i place of (−−T−BINAP. After sufficiently replacing the inside atmosphere of the tube with nitrogen, 60 ml of methylene chloride was added thereto. Then, after adding a solution of 0.36 g (3.0 mmoles) of sodium perhydrochloride dissolved in 60 ml of water and a solution of 16 mg (0.06 mmole) of triethylbenzylammonium bromide dissolved in 3 ml of water to the mixture, the resultant mixture was stirred for 12 hours at room temperature to perform reaction. After completion of the reaction, the reaction mixture was allowed to stand, and an aqueous layer thus formed was removed by liquid separation. The methylene chloride was distilled off under reduced pressure, and the residue was dried under reduced pressure to provide 0.59 g of [Ru((+)−T−BINAP)]-(ClO$_4$)$_2$ as a dark brown solid. The yield was 99.6%.

Elemental Analysis for C$_{48}$H$_{40}$Cl$_2$O$_8$P$_2$Ru:

|  | Ru | P | C | H |
|---|---|---|---|---|
| Calculated: | 10.32% | 6.33% | 58.90% | 4.12% |
| Found: | 10.08% | 5.97% | 58.61% | 4.53% |
| $^{31}$P NMR (CDCl$_3$) δppm: | 12.920 (d, J = 41.1 Hz),<br>61.402 (d, J = 41.1 Hz) | | | |

Example 1

Production of (2S)-(+)-2-methylbutyric acid:

In a 100 ml stainless steel autoclave, the inside atmosphere of which had previously been replaced with argon, were placed 0.2 g (2 mmoles of (E)-2- methyl-2-butenoic acid and 20 ml of methanol and then, 6.0 mg (0.007 mmole) of [Ru((−)−-BINAP](BF$_4$)$_2$ prepared in Referential Example 5 was added to the mixture to perform hydrogenation for 12 hours at a hydrogen pressure of 4 kg/cm$^2$ and at a reaction temperature of 20° C. Thereafter, the solvent was distilled off to provide 0.2 g of 2-methylbutyric acid. The yield thereof was 100%.

Boiling Point: 50° C./0.07 mmHg
$^1$H NMR (CDCl$_3$) δppm:0.95 (t, 3H), 1.17 (d, 3H), 1.15-2.00 (m, 2H), 2.4 (m, 1H), 9.76 (s, 1H)
Specific Rotation: [α]$_D^{25}$ = +18.05° (neat)

Then, an amide was synthesized form the carboxylic acid thus obtained and (R)-(+)-(1-naphthyl)ethylamine, and a high-performance liquid chromatographic analysis was performed. As the result, The original carboxylic acid was found to be a mixture of 95.8% of (2S)−(+)−2-methylbutyric acid and 4.2% of (2R)−(−)−2−methylbutyric acid, and the optical yield of (2S)−(+)−2−methylbutryic acid was 91.6 % ee.

EXAMPLE 2

Production of (2R)−(−)-2-methylbutric acid:

In a 100 ml stainless steel autoclave, the inside atmosphere of which had previously been replaced with argon, were placed 0.2 g (2 mmoles) of (E)-2-methyl-2-butenoic acid, 0.39 g (2 mmoles) of dicyclohexylmethylamine, 2 ml of tetrahydrofuran, and 20 ml of ethanol, Then, 6.3 mg (0.004 mmole) of Ru$_4$Cl$_4$((+)-BINAP)$_2$NEt$_3$) prepared by the same manner as in Referential Example 1 except using (+)-BINAP in place of (−)-T-BINAP was added to the mixture to perform hydrogenation for 12 hours at a hydrogen pressure of 4 kg/cm$^2$ and at a reaction temperature of 0° C. Thereafter, the solvent was distilled off to provide 0.2 g of 2-methylbutyric acid. The yield was 100%.

Specific Rotation: $[\alpha]_D^{25}= -17.30°$ (neat)

An amide was prepared using the aforesaid carboxylic acid and analyzed by the same manner as in Example 1. As the result, the optical yield of (2R)—(−)-2-methylbutyric acid was 57.9% ee.

EXAMPLE 3

Production of (2R)-(−)-2-methylbutric acid:

In a 100 ml stainless steel autoclave, the inside atmosphere of which had previously been replaced with argon, were placed 0.2 g (2 mmoles) of (E)-2-methyl-2-butenoic acid, 0.2 g (2 mmoles) of triethylamine, 2 ml of tetrahydrofuran, and 20 ml of ethanol. Then, 6.9 mg (0.005 mmole of RuHCl((+)-BINAP)$_2$ prepared in Referential Example 2 was added to the mixture to perform hydrogenation for 14 hours at a hydrogen pressure of 30 kg/cm$^2$ and at a reaction temperature of 80° C. Thereafter, the solvent was distilled off to provide 0.2 g of 2-methylbutyric acid. The yield was 100%.

Specific Rotation: $[\alpha]_D^{25}= -15.6°$ (neat)

An amide was prepared using the aforesaid carboxylic acid and analyzed by the same manner as in Example 1. As the result, the optical yield of (2R)-(−)-2-methylbutyric acid was 77.0% ee.

EXAMPLE 4

Production of (2S)-(+)-2-methylbutyric acid:

In a 100 ml autoclave, the inside atmosphere of which had previously been replaced with argon, were placed 0.2 g (2 mmoles) of (Z)-2-methyl-2-butenoic acid, 20 ml of methanol, and 0.39 g (2 mmoles) of dicyclohexylmethylamine to form a solution. Then, 3.4 mg (0.004 mmole) of Ru((+)-BINAP)(O$_2$CCH$_3$)$_2$ prepared according to the same manner as in Referential Example 3 except using (+)-BINAP in place of (−)-BINAP was added to the mixture to perform hydrogenation with stirring for 4 hours at a hydrogen pressure of 125 kg/cm$^2$ and at a reaction temperature of 25° C. Thereafter, the solvent was distilled to provide 0.2 g of 2-methylbutyric acid. The yield was 100%.

Specific Rotation: $[\alpha]_D^{25}= +12.25°$ (neat)

An amide was prepared using the aforesaid carboxylic acid and analyzed by the same manner as in Example 1. As the result, the optical yield of (2S)-(+)-2methylbutyric acid was 57.9% ee.

EXAMPLE 5

Production of (2S)-(+)-2-methylvaleric acid

In a 100 ml autoclave, the inside atmosphere of which had previously been replaced with argon, were placed 0.23 g (2 mmoles) of (E)-2-methyl-2-pentenoic acid and 20 ml of methanol. Then, 8.4 mg (0.01 mmole) of Ru((−)-BINAP)(O$_2$CCH$_3$)$_2$ prepared in Referential Example 3 was added to the mixture to perform hydrogenation for 24 hours at a hydrogen pressure of 4 kg/cm$^2$ and at a reaction temperature of 25° C. Thereafter, the solvent was distilled off to provide 0.23 g of 2-methylvaleric acid. The yield was 100%.

Boiling Point: 50° C./0.07 mmHg $^1$H NMR (CDCl$_3$) δppm: 0.92 (t, 3H), 1.18 (d, 3H), 5 (m, 2H), 1.6–1.75 1.3–1. (m, 1H), 2.48 (m, 1H), 11.00 (s, 1H).

Specific Rotation: $[\alpha]_D^{25}= +14.40°$ (neat)

An amide was prepared using the aforesaid carboxylic acid and analyzed by the same manner as in Example 1. As the result, the optical yield of (2S)-(+)-2-methylvaleric acid was 77.9% ee.

EXAMPLE 6

Production of (2R)-(−)-2-methylphenylacetic acid:

In a 100 ml autoclave, the inside atmosphere of which had previously been replaced with argon, were placed 0.3 g (2 mmoles) of 2-methylenephenylacetic acid and 20 ml of methanol. Then, 8.4 mg (0.01 mmole) of Ru-((+)-BINAP)(O$_2$CCH$_3$)$_2$ prepared according to the same manner as in Referential Example 3 except using (+)-BINAP in place of (−)-BINAP was added to the mixture to perform hydrogenation for 24 hours at a hydrogen pressure of 100 kg/cm$^2$ and at a reaction temperature of 30° C. to provide 0.3 g of 2-methylphenylacetic acid. The yield was 100%.

Boiling Point: 120° C./0.07 mmHg.

$^1$H NMR (CDCl$_3$) δppm: 1.51 (d, 3H), 3.73 (q, 2H), 7.31–7.33 (m, 5H), 14.05 (s, 1H).

Specific Rotation: $[\alpha]_D^{25}= -68.37°$ (c=1.72, chloroform)

An amide was prepared using the aforesaid carboxylic acid and analyzed by the same manner an in Example 1. As the result, the optical yield of (2R)-(-)-2-methylphenylacetic acid was 91.0% ee.

EXAMPLE 7

Production of (2R)-(−)-2-methylnonanoic acid:

In a 200 ml autoclave, the inside atmosphere of which had previously been replaced with argon, were placed 3.0 g (17.6 mmoles) of 2-methylenenonanoic acid and 50 ml of ethanol. Then, 6.9 mg (0.007 mmole) of [Ru((−)-T-BINAP)](ClO$_4$)$_2$ prepared according to the same manner as in Referential Example 6 except using (−)-T-BINAP in place of (+)-T-BINAP was added to the mixture to perform hyd-ogenation for 15 hours at a hydrogen pressure of 30 kg/cm$^2$ and at a reaction temperature of 20° C. Thereafter, the solvent was distilled off to provide 3.0 g of 2-methylnonanoic acid. The theoretical yield (hereafter simply referred to as "yield") was 100%.

Boiling point: 110°–112° C./2 mmHg.

$^1$H NMR (CDCl$_3$) δppm: 0.85–1.80 (m, 18H), 2.24–2.75 (m, 1H), 11.90 (s, 1H)

Specific Rotation: $[\alpha]_D^{20} = -5.40°$ (c=2.11, ethanol)

An amide was prepared using the aforesaid carboxylic acid and analyzed by the same manner as in Example 1. As the result, the optical yield of (2R)-(−)-2-methylnonanoic acid was 37% ee.

EXAMPLE 8

Production of (2R)-(−)-2,3-diphenylpropanoic acid:

In a 100 ml autoclave, the inside atmosphere of which had previously been replaced with argon, were placed 0.45 g (2 mmoles) of (E)-2-phenylcinnamic acid and 20 ml of ethanol, then, 11.2 mg (0.013 mmole) of Ru((-}-BINAP)-(O$_2$CCH$_3$)$_2$ prepared in Referential Example 3 was added to the mixture to perform hydrogenation for 100 hours at a hydrogen pressure of 4 kg/cm$^2$ and at a reaction temperature of 40° C. Thereafter, the solvent was distilled off to provide 0.45 g of 2,3-diphenylpropanoic acid. The yield was 100%.

Boiling Point: 230° C./0.07 mmHg.

$^1$H NMR (CDCl$_3$) δppm: 3.03 (d of d, 1H), 3.41 (d of d, 1H), 3.86 (d of d, 1H), 7.07–7.40 (m, 10H), 15.2 (s, 1H).

Specific Rotation: $[\alpha]_D^{25} = -54.05°$ (c=0.52, acetone)

An amide was prepared using the aforesaid carboxylic acid and analyzed by the same manner as in Example 1. As the result, the optical yield of (2R)-(−)-2,3-diphenylpropanoic acid was 40.5% ee.

EXAMPLE 9

Production of (3S)-(−)-citronellic acid:

In a 100 ml autoclave, the inside atmosphere of which had previously been replaced with argon, were placed 0.34 g (2 mmoles) of geranic acid, 20 ml of methanol, and 0.39 g (2 mmoles) of dicyclohexylmethylamine. Then, 5.6 mg (0.007 mmole) of Ru((+)-BINAP)-(O$_2$CCH$_3$)$_2$ prepared according to the same manner as in Referential Example 3 except using (+)-BINAP in place of (−)-BINAP was added to the mixture to perform hydrogenation for 12 hours at a hydrogen pressure of 100 kg/cm$^2$ and at a reaction temperature of 25° C. Thereafter, the solvent was distilled off to provide 0.34 g of citronellic acid.

Boiling Point: 100° C./0.07 mmHg.

$^1$H NMR (CDCl$_3$) δppm: 0.97 (d, 3H), 1.1–1.5 (m, 2H), 1.60 (s, 3H), 1.67 (s, 3H), 1.73–2.50 (m, 4H), 5.08 (t, 1H), 12.30 (s, 1H).

Specific Rotation: $[\alpha]_D^{25} = -7.82°$ (c=2.99, methanol)

An amide was prepared using the aforesaid carboxylic acid and analyzed by the same manner as in Example 1. As the result, the optical yield of (3S)-(−)-citronellic acid was 87.0% ee.

EXAMPLE 10

Production of naproxen
(6-methoxy-o-methyl-2-naphthaleneacetic acid):

In a 100 ml autoclave, the inside atmosphere of which had previously been replaced with argon, were placed 0.45 g (2 mmoles) of 6-methoxy-α-methylene-2-naphthaleneacetic acid, 20 ml of methanol, and 0.39 g (2 mmoles) of dicyclohexylmethylamine. Then, 9.0 mg (0.010 mmole) of Ru((−)-T-BINAP)(O$_2$CCH$_3$)$_2$ prepared according to the same manner as in Referential Example 3 except using (−)-T-BINAP in place of (−)-BINAP was added to the mixture to perform hydrogenation for 12 hours at a hydrogen pressure of 135 kg/cm$^2$ and at a reaction temperature of 17° C. Thereafter, the solvent was distilled off to provide 0.39 g of naproxen. The yield was 84%.

Melting Point: 154°–155° C.

$^1$H NMR (CDCl$_3$) δppm: 1.57 (d, 3H), 3.86 (q, 1H), 3.90 (s, 3H), 7.07–7.87 (m, 6H), 10.83 (s, 1H)

Specific Rotation: $[\alpha]_D^{25} = +59.21°$ (c=1.08, chloroform)

An amide was prepared using the aforesaid carboxylic acid and analyzed by the same manner as in Example 1. As the result, the optical yield of naproxen was 90.4% ee.

EXAMPLE 11

Production of naproxen:

In a 100 ml autoclave, the inside atmosphere of which had previously been replaced with argon, were placed 0.45 g (2 mmoles) of 6-methoxy-α-methylene-2-naphthaleneacetic acid and 20 ml of methanol. Then, 3.6 mg (0.004 mmole) of Ru2Cl4((−)-T-BINAP)$_2$(NEt$_3$) prepared in Referential Example 1 was added to the mixture to perform hydrogenation for 24 hours at a hydrogen pressure of 40 kg/cm$^2$ and at a reaction temperature of 20° C. Thereafter, the solvent was distilled off to provide 0.42 g of naproxen. The yield was 92%.

Melting Point: 154°–155° C.

$^1$H NMR (CDCl$_3$) δppm: 1.57 (d, 3H), 3.86 (q, 1H), 3.90 (s, 3H), 7.07–7.87 (m, 6H), 10.83 (s, 1H).

Specific Rotation: $[\alpha]_D^{25} = +49.0°$ (c=1.01, chloroform).

An amide was prepared using the aforesaid carboxylic acid and analyzed by the same manner as in Example 1. As the result, the optical yield of naproxen was 74% ee.

EXAMPLE 12

Production of naproxen:

In a 100 ml autoclave, the inside atmosphere of which had previously been replaced with argon, were placed 0.45 g (2 mmoles) of 6-methoxy-α-methylene-2-naphthaleneacetic acid and 20 ml of methanol. Then, 2.0 mg (0.002 mmole) of Ru((−)-T-BINAP)(O$_2$CCF$_3$)$_2$ prepared in Referential Example 4 was added to the mixture to perform hydrogenation for 24 hours at a hydrogen pressure of 40 kg/cm$^2$ and at a reaction temperature of 20° C. Thereafter, the solvent was distilled off to provide 0.43 g of naproxen. The yield thereof was 93.7%.

Melting Point: 154°–155° C.

$^1$H NMR (CDCl$_3$) δppm: 1.57 (d, 3H), 3.86 (q, 1H), 3.90 (s, 3H), 7.07–7.87 (m, 6H), 10.83 (s, 1H).

Specific Rotation: $[\alpha]_D^{25} = +38.87°$ (c=0.98, chloroform).

An amide was prepared using the aforesaid carboxylic acid and analyzed by the same manner as in Example 1. As the result, the optical yield of naproxen was 58.8% ee.

EXAMPLE 13

Production of (3S)-(+)-3-phenylbutyric acid:

In a 100 ml autoclave, the inside atmosphere of which had previously been replaced with argon, were placed 0.32 g (2 mmoles) of (Z)-3-methylcinnamic acid and 20 ml of methanol. Then, 2.9 mg (0.0034 mmole) of Ru((+)BINAP)-(O$_2$CCH$_3$)$_2$ prepared according to the same manner as in Referential Example 3 except using (+)-BINAP in place of (−)-BINAP was added to the mixture to perform hydrogenation for 70 hours at a hydrogen pressure of 104 kg/cm² and at a reaction temperature of 25° C. Thereafter, the solvent was distilled off to provide 0.32 g of 3-phenylbutyric acid. The yield was 100%.

Boiling Point: 170° C./0.05 mmHg.

¹H NMR (CDCl₃) δppm: 1.30 (d, 3H), 2.57 (d, 1H), 2.60 (d, 1H), 3.27 (m, 1H), 7.32 (broad s, 5H), 12.20 (s, 1H).

Specific Rotation: $[\alpha]_D^{25} = +0.44°$ (c=0.94, benzene).

An amide was prepared using the aforesaid carboxylic acid and analyzed by the same manner as in Example 1. As the result, the optical yield of (3S)-(+)-3-phenylbutyric acid was 84.8% ee.

EXAMPLE 14

Production of (2R)-(−)-2-(p-methoxyphenyl)propionic acid:

In a 100 ml autoclave, the inside atmosphere of which had previously been replaced with argon, were placed 0.36 g (2 mmoles) of p-methoxyatropic acid and 20 ml of methanol. Then, 7.5 mg (0.009 mmole) of Ru((+)-BINAP)-(O₂CCH₃)₂ prepared according to the same manner as in Referential Example 3 except using (+)-BINAP in place of (−)-BINAP was added to the mixture to perform hydrogenation for 12 hours at a hydrogen pressure of 100 kg/cm² and at a reaction temperature of 19° C. Thereafter, the solvent was distilled off to provide 0.32 g of (2R)-(−)-2-(p-methoxyphenyl)propionic acid. The yield was 89%.

Boiling Point: 220° C./0.05 mmHg.

¹H NMR (CDCl₃) δppm: 1.49 (d, 3H), 3.71 (q, 1H), 3.82 (s, 3H), 6.88 (d, 2H), 7.28 (d, 2H), 11.3 (broad s, 1H).

Specific Rotation: $[\alpha]_D^{25} = -53.91°$ (c=1.02, ethanol).

An amide was prepared using the aforesaid carboxylic acid and analyzed by the same manner as in Example 1. As the result, the optical yield of (2R)-(−)-2-(p-methoxyphenyl)propionic acid was 83.0% ee.

As described above, in this invention, by asymmetrically hydrogenating α,β-unsaturated carboxylic acids using a ruthenium-optically active phosphine complex as a catalyst, optically active carboxylic acids which can be widely used as raw materials for synthesizing various useful compounds, for example, as intermediates for synthesizing physiologically active substances of natural materials and also as liquid crystal materials can be industrially advantageously produced.

While the invention has been described in detail and with reference to specific embodiments thereof, it will be apparent to one skilled in the art that various changes and modifications can be made therein without departing from the spirit and scope thereof.

What is claimed is:

1. A process for producing an optically active carboxylic acid represented by formula (I):

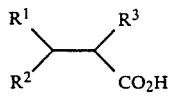

wherein R¹, R² and R³ are each selected from the group consisting of a hydrogen atom, an alkyl group, an alkenyl group, a phenyl group, a substituted phenyl group, a naphthyl group and a substituted naphthyl, wherein said substituted phenyl and said substituted naphthyl are substituted with a member selected from the group consisting of a hydroxyl group, a methoxy group, an amino group, a dimethylamino group, a chlorine atom, and a bromine atom, provided that all of R¹, R² and R³ do not simultaneously represent a hydrogen atom; and when R¹ and R² simultaneously represent a hydrogen atom, then R³ is not a methyl group; and that when R³ is a hydrogen atom, then R¹ and R² are each a group other than a hydrogen atom; which process comprises:

asymmetrically hydrogenating an α, -unsaturated carboxylic acid represented by formula (II):

wherein R¹, R², and R³ are the same as defined above, in the presence of a ruthenium-optically active phosphine complex represented by formula (V) or (VII), below, as a catalyst

wherein X—R⁵—BINAP signifies a tertiary phosphine of formula (VI):

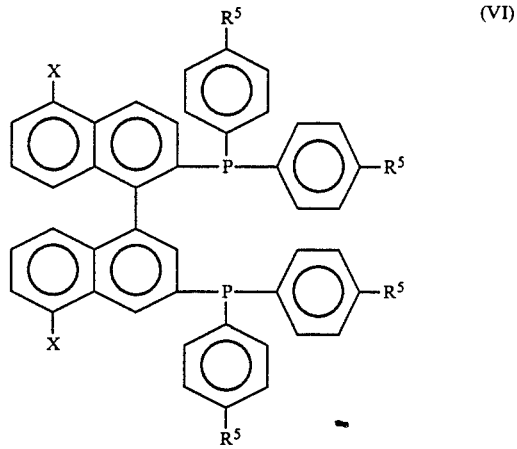

in which X represents a hydrogen atom, an amino group, an acetylamino group, or a sulfo group; R⁵ represents a hydrogen atom or a lower alkyl group; R⁶ and R⁷ each represents an alkyl group, a halogenated lower alkyl group, a phenyl group, a phenyl group substituted with a lower alkyl group, an α-aminoalkyl group, or an α-aminophenylalkyl group, or R⁶ and R⁷ are taken together to form an alkylene group; and q represents 1 or 2;

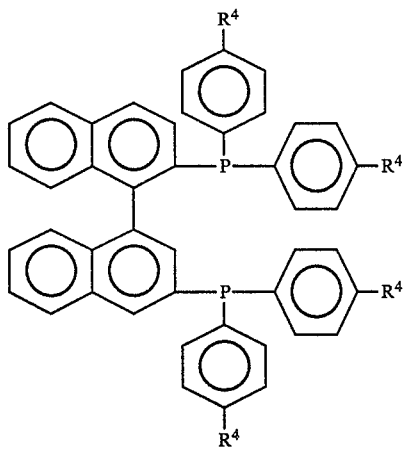

(IV)

in which $R^4$ is a hydrogen atom or a methyl group; Y is $ClO_4$, $BF_4$, or $PF_6$; when l is 0, then v is 1 and w is 2; and when l is 1, then v is 2 and W is 1.

2. A process as in claim 1, wherein said ruthenium-optically active phosphine complex is represented by formula (VII):

$$[Ru(X\text{—}R^5\text{—}BINAP)_q](O\overset{O}{\overset{\|}{C}}R^6)(O\overset{O}{\overset{\|}{C}}R^7) \quad (V)$$

wherein $R^4$-BINAP signifies a tertiary phosphine of formula (VI):

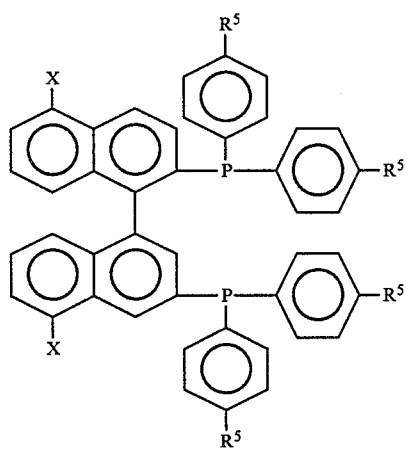

(VI)

in which X represents a hydrogen atom, an amino group, an acetylamino group, or a sulfo group; $R^5$ represents a hydrogen atom or a lower alkyl group; $R^6$ and $R^7$ each represents an alkyl group, a halogenated lower alkyl group, a phenyl group, a phenyl group substituted with a lower alkyl group, an α-aminoalkyl group, or an α-aminophenylalkyl group, or $R^6$ and $R^7$ are taken together to from an alkylene group, and q represents 1 or 2.

3. A process as in claim 2, wherein said ruthenium-optically active phosphine complex is selected from among the following:

Ru(BINAP)(O₂CCH₃)₂;
Ru(BINAP)(O₂CCF₃)₂;
Ru(T-BINAP)₂(O₂CCF₃)₂;
Ru(T-BINAP)₂(O₂CCH₃)₂;
Ru(BINAP)(O₂Ct-Bu)₂;
Ru(BINAP)(O₂CPh)₂;
Ru(T-BINAP)(O₂CCH₃)₂;

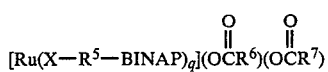

Ru(T-BINAP)(O₂CCF₃)₂;
Ru(t-BuBINAP)(O₂CCH₃)₂;
Ru(amino BINAP)(O₂CCH₃)₂;
Ru(acetylamino BINAP)(O₂CCH₃)₂;
Ru(sulfonated BINAP)(O₂CCH₃)₂;

$$Ru(BINAP)(O\overset{\|}{\underset{O}{C}}(CH_2)_3\overset{\|}{\underset{O}{C}}O);$$

Ru(BINAP)(O₂CCHCH₂Ph)₂; and
　　　　　　　　|
　　　　　　　NH₂

Ru(BINAP)(O₂CCH-i-Pr)₂,
　　　　　　　|
　　　　　　NH₂ wherein i-Pr signifies an isopropyl group; Ph signifies a phenyl group; BINAP signifies 2,2'-bis(diphenylphosphino)-1,1'-binaphthyl; T-BINAP signifies 2,2'-bis(di-p-tolylphosphino)-1,1'-binaphthyl; t-BuBINAP signifies 2,2'-bis-(di-p-t-butylphenylphosphino)-1,1'-binaphthyl; sulfonated BINAP signifies 2,2'-bis(diphenylphosphino)-5,5'-bis-(sodium sulfonate)-1,1'-naphthyl; amino BINAP signifies 2,2'-bis(diphenylphosphino)-5,5'-bis-(amino)-1,1'-binaphthyl; and acetylamino BINAP signifies 2,2'-bis(diphenylphosphino)-5,5'-bis(acetylamino)-1,1'-binaphthyl.

4. The process as in claim 2, wherein the lower alkyl group for $R^5$ is an alkyl group having from 1 to 4 carbon atoms; the alkyl group for $R^6$ and $R^7$ is an alkyl group having from 1 to 9 carbon atoms; the alkyl group in the αaminoalkyl group for $R^6$ and $R^7$ is an alkyl group having from 1 to 4 carbon atoms; and the alkyl group in the α-aminophenyl alkyl group for $R^6$ and $R^7$ is an alkyl group having from 1 to 4 carbon atoms.

5. A process as in claim 1, wherein said ruthenium-optically active phosphine complex is represented by formula (VII):

$$[RuH_l(R^4\text{—}BINAP)_v]Y_w \quad (VII)$$

wherein $R^4$—BINAP signifies a tertiary phosphine of formula (IV):

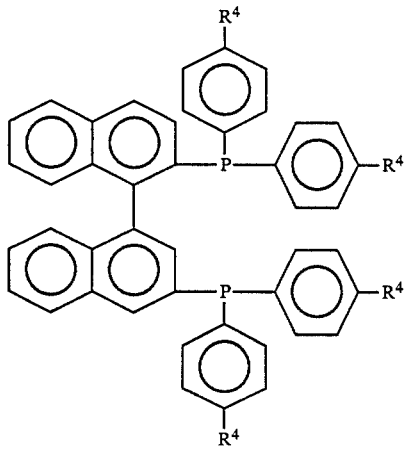

(IV)

in which R⁴ is a hydrogen atom or a methyl group; Y is ClO₄, BF₄, or PF₆; when l is 0, then v 1 and w is 2; and when l is 1, then v is 2 and w is 1.

6. A process as in claim 8, wherein said ruthenium-optically active phosphine complex is selected from among the following:
Ru(T-BINAP)](BF₄)₂;
RuH(T-BINAP)2]BF₄;
Ru(BINAP)](BF₄)₂;
Ru(BINAP)](ClO₄)₂;
Ru(T-BINAP)](ClO₄)₂;
Ru(T-BINAP)](PF₆)₂;
RuH(BINAP)₂]BF₄;
RuH(T-BINAP)₂]ClO₄; and
RuH(T-BINAP)hd ]PF₆,
wherein BINAP signifies 2,2'-bis(diphenylphosphino)-1,1'-binaphthyl, and T-BINAP signifies 2,2'-bis(di-p-tolylphosphino)-1,1'-binaphthyl.

7. A process as claimed in claim 1, wherein the alkyl group is an alkyl group having from 1 to 7 carbon atoms; and the alkenyl group is an alkenyl group having from 3 to 6 carbon atoms.

* * * * *

UNITED STATES PATENT AND TRADEMARK OFFICE
CERTIFICATE OF CORRECTION

PATENT NO. : 4,962,230  
DATED : October 9, 1990  
INVENTOR(S) : Hidemasa Takaya et al Page 1 of 3

It is certified that error appears in the above-indentified patent and that said Letters Patent is hereby corrected as shown below:

Cols. 4,17 (Claim 1) and 19 (Claim 5), delete

"                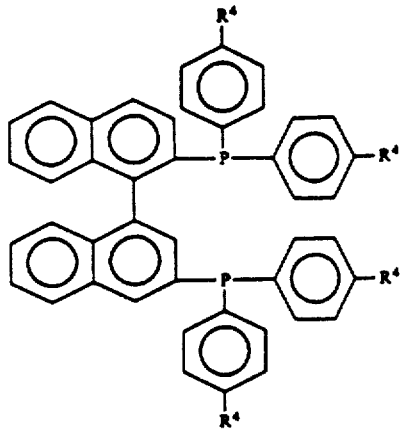                (IV)                "

and insert

--                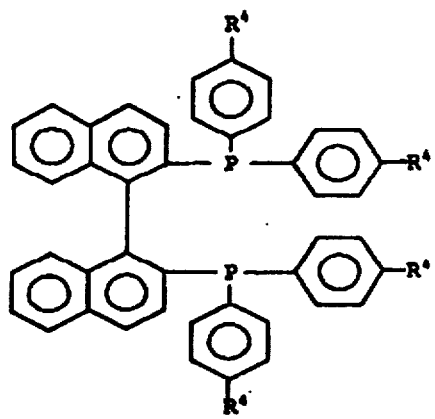                (IV)                --

UNITED STATES PATENT AND TRADEMARK OFFICE
CERTIFICATE OF CORRECTION

PATENT NO. : 4,962,230
DATED : October 9, 1990
INVENTOR(S) : Hidemasa Takaya et al It is certified that error appears in the above-indentified patent and that said Letters Patent is hereby corrected as shown below:

Cols. 5, 16 (Claim 1) and 17 (Claim 2), delete

" 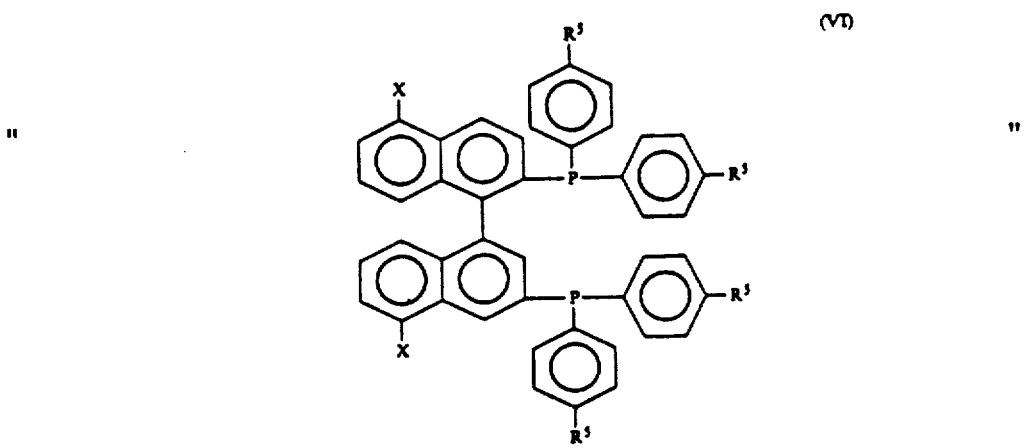 "

and insert

-- 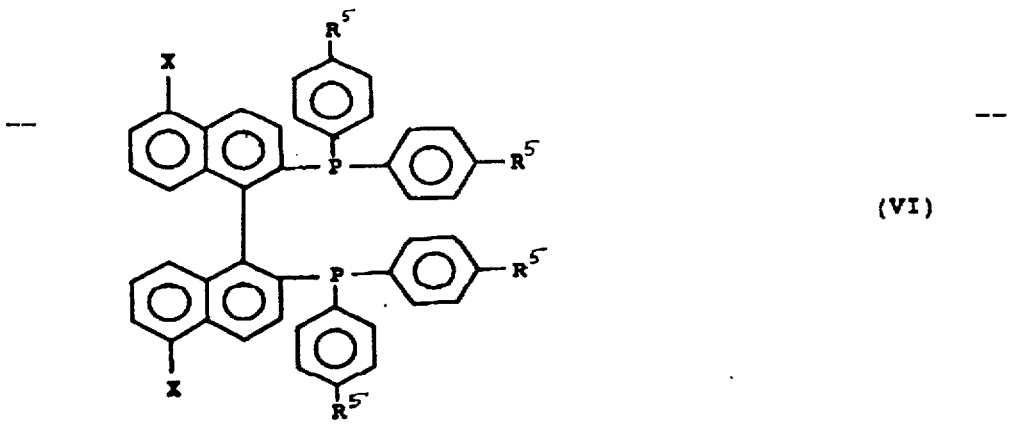 --

UNITED STATES PATENT AND TRADEMARK OFFICE
CERTIFICATE OF CORRECTION

PATENT NO. : 4,962,230
DATED : October 9, 1990
INVENTOR(S) : Hidemasa Takaya et al It is certified that error appears in the above-indentified patent and that said Letters Patent is hereby corrected as shown below:

Col. 17, line 25, delete "(VII)" and insert --(V)--;

Col. 17, line 31, delete "$R^4$-BINAP" and insert --X-$R^5$-BINAP--;

Col. 20, line 4, delete "claim 8" and insert --claim 5--.

Signed and Sealed this

Twenty-sixth Day of October, 1993

*Attest:*

BRUCE LEHMAN

*Attesting Officer*    Commissioner of Patents and Trademarks